United States Patent [19]

Hess

[11] Patent Number: 4,841,971
[45] Date of Patent: Jun. 27, 1989

[54] ENDOCARDIAL LEAD WITH PROJECTIONS HAVING SAW TOOTH FORMATION

[75] Inventor: Stanley R. Hess, Miami, Fla.

[73] Assignee: Cordis Leads, Inc., Miami, Fla.

[21] Appl. No.: 172,967

[22] Filed: Mar. 29, 1988

Related U.S. Application Data

[63] Continuation of Ser. No. 56,472, May 26, 1987, abandoned, which is a continuation of Ser. No. 783,820, Oct. 7, 1985, abandoned, which is a continuation of Ser. No. 502,225, Jun. 8, 1983, abandoned, which is a continuation-in-part of Ser. No. 311,620, Oct. 15, 1981, abandoned.

[51] Int. Cl.$^4$ ............................................. A61N 1/04
[52] U.S. Cl. .................................. 128/419 P; 128/785
[58] Field of Search .................... 128/419 P, 784, 785, 128/788

[56] References Cited

U.S. PATENT DOCUMENTS

| | | | |
|---|---|---|---|
| 2,668,387 | 2/1954 | Gallardo | 43/44.4 |
| 3,844,292 | 10/1974 | Bolduc | 128/418 |
| 3,902,501 | 9/1975 | Citron et al. | 128/418 |
| 3,902,502 | 9/1975 | Citron et al. | 128/418 |
| 4,033,357 | 7/1977 | Helland et al. | 128/418 |
| 4,301,815 | 11/1981 | Dorig | 128/419 P X |
| 4,360,031 | 11/1982 | Whike | 128/419 P X |
| 4,402,328 | 9/1983 | Doring | 128/785 |
| 4,409,994 | 10/1983 | Doring | 128/785 |
| 4,454,888 | 6/1984 | Gold | 128/785 |
| 4,467,817 | 8/1984 | Harris | 128/419 P X |

Primary Examiner—Edward M. Coven
Attorney, Agent, or Firm—Henry W. Collins; Thomas R. Vigil

[57] ABSTRACT

The endocardial lead comprises an elongate electrical conductor extending substantially the length of the lead, an insulating sheath surrounding the conductor for substantially the entire length of the conductor, and an electrode assembly at the distal end of the lead. The electrode assembly comprises a tip electrode having a distal tip and a proximal end and a sleeve of insulating material extending between and surrounding the proximal end of the tip electrode and the distal end of both the insulating sheath and the elongate conductor with the distal end of the elongate conductor being electrically connected to the proximal end of the tip electrode within the sleeve. The sleeve has at least two circumferentially spaced projections, each projection extending radially and axially away from the outer surface of the sleeve rearwardly away from the distal tip. Each projection has a rear edge and at least one saw tooth which extends radially outwardly of the axis of the electrode assembly, whereby, when the electrode assembly at the distal end of the lead is implanted within a heart, the rear edge of the projection and the at least one saw tooth engage and become attached to trabeculae within a heart cavity thereby to aid in retaining the distal tip of the tip electrode in good electrical conductive engagement with a desired wall portion in the heart cavity.

28 Claims, 2 Drawing Sheets

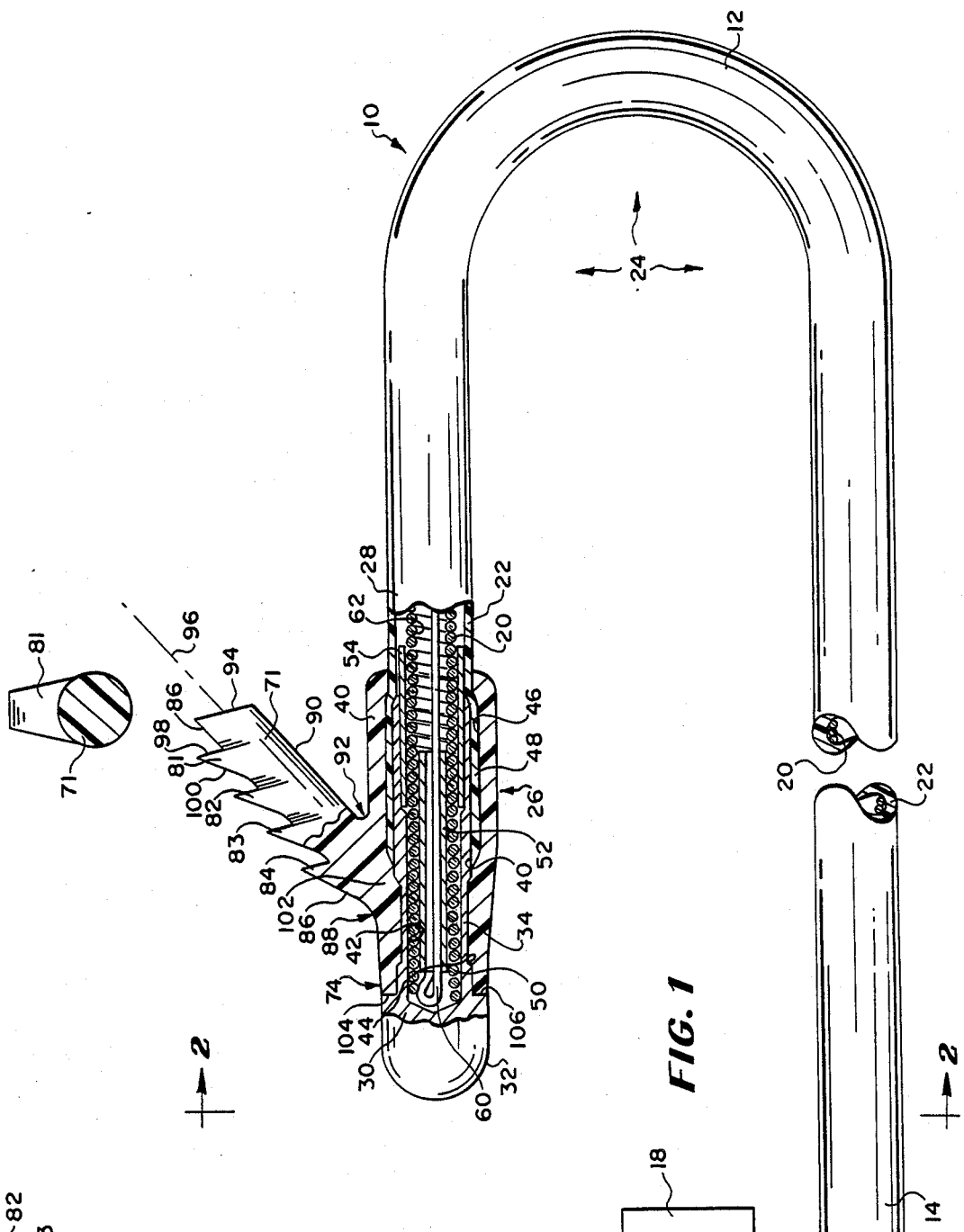
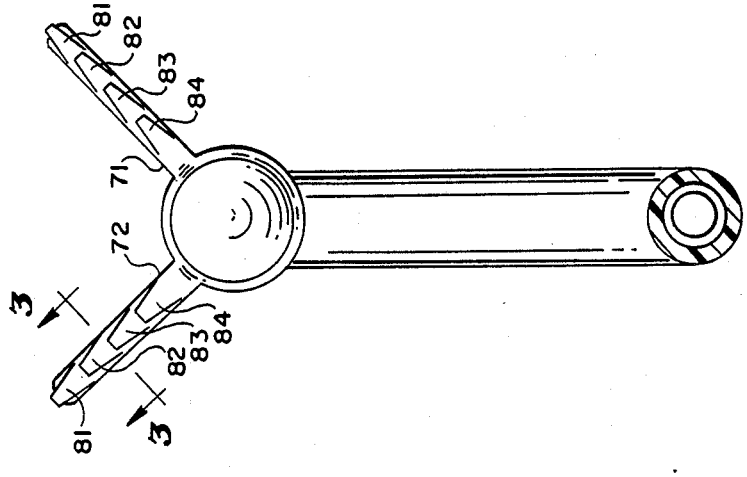
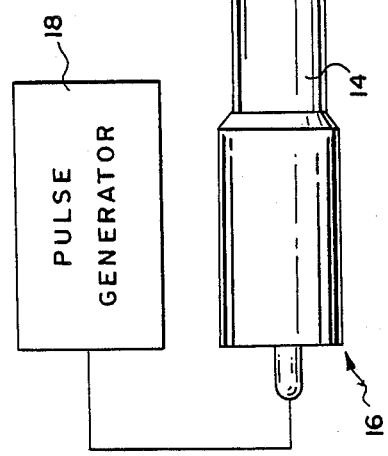

ENDOCARDIAL LEAD WITH PROJECTIONS HAVING SAW TOOTH FORMATION

CROSS REFERENCE TO RELATED APPLICATION

This is a continuation of application Ser. No. 056,472, filed May 26, 1987 which is a continuation of application Ser. No. 783,820 filed Oct. 7, 1985, now abandoned; which is a continuation of application Ser. No. 502,225 filed June 8, 1983, now abandoned; which is a continuation-in-part of application Ser. No. 311,620 filed Oct. 15, 1981, which is now abandoned.

BACKGROUND OF THE INVENTION

1. Field of the Invention

The present invention relates to an endocardial lead adapted to be implanted within a chamber in a human organ, such as the heart, with the lead comprising a lead body and an electrode assembly having projections extending therefrom with saw teeth on the projections which can be in the form of tines or fins, for enhancing, facilitating and enabling the electrode assembly to lodge itself in trabeculae in heart chamber, such as the atrium or ventricle, for holding the electrode assembly in a desired position where an electrode tip of the assembly bears against and makes good electrical contact with an endocardial wall of the heart chamber.

2. Description of the Prior Art

Heretofore, it has been proposed to provide a transvenous body implantable lead having a tip electrode at the distal end thereof and having tines extending from a sheath of a lead body just behind the tip electrode. These tines extend angularly, rearwardly and outwardly from the sheath.

A leading example of such a transvenous body implantable lead is disclosed in U.S. Pat. No. 3,902,501 issued to Paul Citron and Eugene A. Dickhudt on Sept. 2, 1975, the disclosure of which patent is incorporated herein by reference.

Another example of such a transvenous body implantable lead is disclosed in U.S. Pat. No. 3,939,843 issued to Nicholas P.D. Smyth on Feb. 24, 1976 the disclosure of which patent is incorporated herein by reference.

The lead of the Smyth patent can have from 3 to 9 tines with the tines arranged axially and circumferentially around the lead body at the distal end thereof. Such tines are made of a plastic flexible material so that they can bend rearwardly, downwardly when the lead body is inserted through a vein to a heart chamber.

It has also been proposed to provide an electrode having a metal barbed electrode tip with a barb extending rearwardly of the tip. Such electrode tip is part of an electrode assembly mounted on the end of a myocardial sutureless unipolar lead and the barbed electrode tip is adapted to be inserted through the outer wall of the heart and embedded in the heart wall tissue.

Also, it is known of course, to provide saw teeth on saw blades and in devices utilized to hold bait, such as in an animal trap, a mouse trap or a fish hook assembly.

However, heretofore it has not been proposed to provide at least one saw tooth or a saw teeth formation on an outer facing edge of a projection projecting from an insulating sleeve of a distal electrode assembly mounted at the distal end of an endocardial lead.

As will be described in greater detail hereinafter, the endocardial lead of the present invention and particularly, the electrode assembly at the distal end thereof, differs from the electrode tip and tine construction at the distal end of the transvenous lead disclosed in the Smyth U.S. Pat. No. 3,939,843 by providing projections at the distal end of the lead that have at least one saw tooth or saw teeth formations thereof, the projections being in the form of tines or fins.

SUMMARY OF THE INVENTION

According to the invention there is provided an endocardial lead comprising an elongate electrical conductor extending substantially the length of said lead; an insulating sheath surrounding said conductor for substantially the entire length of said conductor; an electrode assembly at the distal end of said lead; said electrode assembly comprising a tip electrode having a distal tip and a proximal end and a sleeve of insulating material extending between and surrounding said proximal end of said tip electrode and the distal end of both said insulating sheath and said elongate conductor with the disal end of said elongate conductor being electrically connected to said proximal end of said tip electrode within said sleeve; and said sleeve having at least two circumferentially spaced projections, each projection extending radially and axially away from the outer surface of said sleeve rearwardly away from said distal tip and each projection having a rear edge and at least one saw tooth which extends radially outwardly of the axis of said electrode assembly, whereby, when said electrode assembly at the distal end of said lead is implanted within a heart, said rear edge of said projection and said at least one saw tooth engage and become attached to trabeculae within a heart cavity thereby to aid in retaining said distal tip of said tip electrode in good electrical conductive engagement with a desired wall portion in the heart cavity.

BRIEF DESCRIPTION OF THE DRAWINGS

FIG. 1 is an enlarged side elevational view of the endocardial lead of the present invention having a J-shaped distal end portion and with portions broken away of the electrode assembly of the lead to show the construction thereof according to the teachings of the present invention.

FIG. 2 is a sectional view of a portion of the lead body of the lead shown in FIG. 1 and of the front end or tip of the electrode assembly at the distal end of the lead body and is taken along line 2—2 of FIG. 1.

FIG. 3 is a sectional view through one saw tooth tine and is taken along line 3—3 of FIG. 2.

DESCRIPTION OF THE PREFERRED EMBODIMENT

Figure 4:
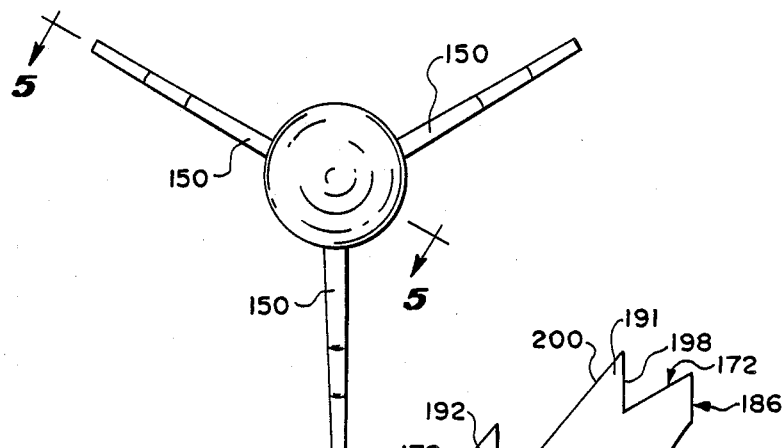
FIG. 4 is a front end view of another electrode assembly constructed according to the teachings of the present invention with three saw tooth fins.

Referring now to the drawings in greater detail there is illustrated in FIG. 1 an endocardial pacing lead 10 comprising a lead body 12. As shown, a proximal end 14 of the lead body 12 has a terminal electrode assembly 16 thereon which is adapted to be connected to a pulse generator 18, typically mounted within a pacer or pacemaker unit (not shown).

The lead body 12 includes a coiled single or multi-wire conductor 20 which extends the length of the lead body 12 and a surrounding tubular sheath 22 of insulating material.

The endocardial lead 10 shown in FIG. 1 is of the type which has a J-shaped end portion 24 with an electrode assembly 26 at the distal end 28 of the lead body 12. The electrode assembly 26 includes a tip electrode 30 having a bullet shaped tip 32 at the distal end thereof and a tubular shank 34 extending rearwardly therefrom at the proximal end thereof. Received around the tubular shank 34 is a sleeve 40 of insulating material which is constructed in accordance with the teachings of the present invention.

As shown in FIG. 1, the sleeve 40 has formed in the hollow interior thereof a smaller in diameter portion 42 which is received in a wide annular groove 44 in the outer surface of the shank 34 for holding the sleeve 40 on the shank 34 and a larger in diameter cavity forming portion 46 in which is received the distal end 48 of the insulative sheath 22 between the interior of the sleeve 40 and the outer surface of the tubular shank 34.

A bared distal end 50 of the coiled conductor 20 extends within the hollow interior of the tubular shank 34 and about a metal tube 52 and within a larger metal sleeve 54. The metal tube 52, the metal sleeve 54 and the tubular shank 34 cooperates to hold the bared distal end 50 of the conductor 20 in mechanical and electrical contact with each other thereby to provide a good electrical contact between bared conductor distal end 50 and the tip electrode 30.

Also as shown, a stylet 60 is received through a lumen 62 defined by and within the coiled conductor 20 and through the metal tube 52 for facilitating manipulation of the electrode assembly 26 once the electrode assembly 26 and lead body 12 have been inserted through a blood vessel to position the electrode assembly 26 in a heart cavity such as the atrium.

In accordance with the teachings of the present invention, and as shown in FIGS. 1, 2 and 3, the insulating sleeve 40 of the distal electrode assembly 26 has at least one and preferably, as shown, two, identical projections 71 and 72 in the form of tines 71 and 72 which extend radially outwardly and axially rearwardly from an outer surface 74 of the sleeve 40 and away from the distal tip 32 of the tip electrode 30.

As shown in FIG. 2, these tines 71, 72 are spaced circumferentially about the sleeve 40 outer surface 74 from each other by an angle of approximately 90°.

Also, and in accordance with the teachings of the present invention, each tine 71, 72 has at least one saw tooth formation 81 projecting outwardly from the tine 71 or 72 in a direction radially outwardly from the axis of the sleeve 40. As shown, each tine 71, 72 is preferably provided with a four tooth formation hereinafter simply saw teeth 81-84.

Since each of the tines 71 and 72 is identical, only the tine 71 will be described in detail with reference to FIGS. 1, 2 and 3.

As shown, tine 71 extends rearwardly and angularly outwardly from the sleeve 40 at an angle of between 30° and 60° and preferably at an angle of 45°. Also, an upper side 86 of the tine 71, extending at an angle of 45°, is connected to the outer surface 74 of the sleeve 40 by a fillet or round surface 88. Likewise, the underside 90 of the tine 71 is connected to the sleeve surface 74 by a rounded surface or fillet 92.

Each tine, 71, 72, is preferably round in cross section as shown in FIG. 3 and has a diameter of between 0.020 and 0.040 inch and preferably a diameter of 0.032 inch.

It will be appreciated that the sleeve 40 and tines 71, 72 are made of a flexible elastomeric material which permits bending down of the tines 71, 72 when the electrode assembly 26 is moved forwardly and which, when moved rearwardly, permits the tines 71, 72 and saw teeth 81-84 thereon to engage tissue within a heart chamber such as trabeculae in an atrium.

The point of each saw tooth 81-84 is separated from each adjacent saw tooth 81-84 by a distance of approximately 0.05 inch. Also as shown, a rear edge 94 of the tine 71 has a chamfer such that it is at an angle of between 45° and 90° to axis 96 of the tine 71 and is preferably at an angle of approximately 60° to the axis 96 of the tine 71. In similar manner, the back edge, e.g., edge 98, of each saw tooth 81-84 extends at an angle between 45° and 90° to the axis 96 of the tine 71 and preferably at an angle of 60° as shown.

Th front or top edge, e.g., edge 100, of each saw tooth 81-84 is at an angle of between 10° and 30° to the axis 96 of the tine 71 and is preferably at an angle of 20° as shown.

The sleeve 40 has a length of between 0.17 and 0.30 inch and preferably has a length of approximately 0.23 inch. As shown, a base 102 of the tine 71 is located on the sleeve 40 at a point ¼ to ⅓ of the length of the sleeve 40 from a forward edge 104 of the sleeve 40 which abuts a rear edge 106 of the distal tip 32 of the tip electrode 30.

The thickness of the sleeve 40 is between 0.02 inch and 0.04 inch and is preferably approximately 0.03 inch. In one preferred embodiment, the outer diameter of the sleeve 40 is approximately 0.10 inch.

Although only two tines 71, 72 have been shown spaced 90° from each other, three tines can be provided with the middle tine 71 spaced 45° from adjacent tines 71, 72 or all three tines 71, 72 can be spaced 120° from each other.

Accordingly, the arrangement of the tines 71, 72 can be altered to include three tines as described above and the electrode assembly 26 with two or three tines 71, 72 is particularly adapted for use with a J atrial lead where the J shaped end portion 24 of the lead body 12 with the electrode assembly 26 is inserted through a blood vessel into the atrial chamber or atrium of a heart and positioned so that the tines 71, 72 engage trabeculae at the upper end of the heart chamber or atrium and by reason of the engagement of the tines 71, 72 and particularly the rear edge 94 of tines 71, 72 and back edge 98 of the saw teeth 81-84 thereon urge the distal tip 32 of the tip electrode 30 into good electrical conductive engagement with a wall portion, e.g., an endocardial wall portion, of the heart within the atrium.

The dimensions and parameters of the sleeve 40 and the tines 71 and 72 were determined from empirical tests and were found to provide the desired engaging and holding function desired.

Figure 5:
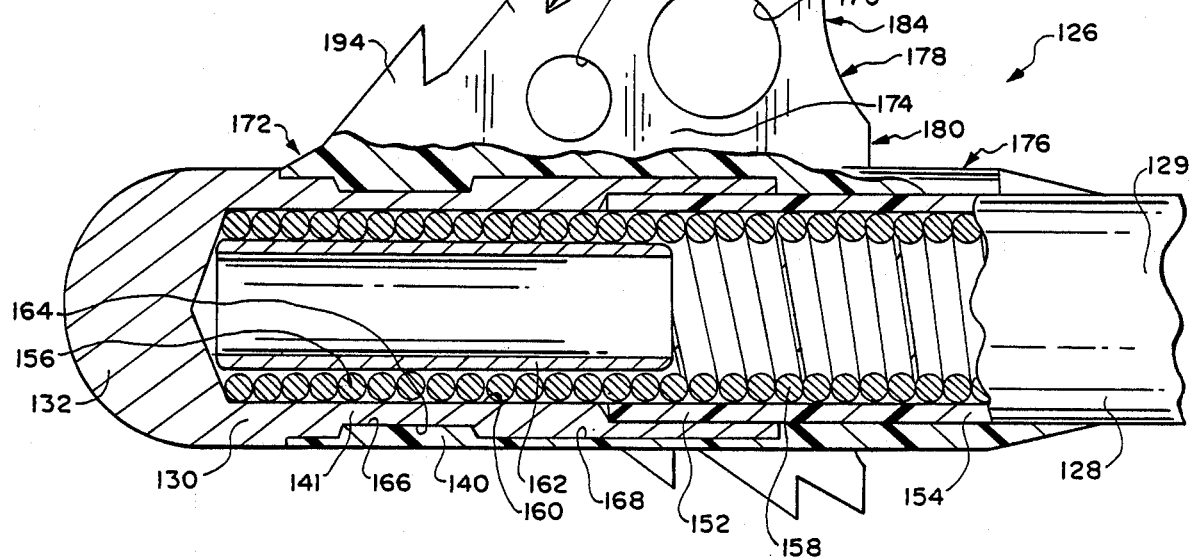
FIG. 5 is a partially sectional view of the electrode assembly in one fin shown in FIG. 4 and is taken along line 5—5 of FIG. 4.

Referring now to FIGS. 4 and 5, there is illustrated therein another embodiment of an electrode assembly 126 constructed according to the teachings of the present invention and adapted for mounting at the distal end 128 of a lead body 129 of an endocardial lead.

The electrode assembly 126 including a tip electrode 130 as shown in FIG. 5 is particularly adapted for insertion into a ventricle for engaging trabeculae in a ventricle for holding the electrode assembly 126 i na desired position with a distal tip 132 of the tip electrode 130 thereof bearing against a desired endocardial wall portion of the heart. In this embodiment, it will be apparent that a sleeve 140 surrounds a shank 141 of the tip electrode 130 and has three identical projections 150 in the form of three fins 150, extending therefrom. Since all the fins 150 are substantaily identical, only one fin 150 is described in detail hereinafter with reference to FIG. 5.

As shown in FIG. 5, the fin 150 extends angularly rearwardly and radially outwardly from the sleeve 140 which surrounds the shank 141 of the tip electrode 130 and a distal end 152 of a sheath 154 of the lead body 129.

In this embodiment, a bared distal end 156 of a single or multi-wire conductor 158 of the lead body 129 is received within a cylindrical cavity 160 within the tubular shank 141 and about a metal tube 162.

The outer surface of the tubular shank 141 has an annular groove 164 therein which receives a mating annular projection 166 extending inwardly from an inner surface 168 of the sleeve 140.

As shown in FIG. 5, each fin 150 has at least two circular openings 170 and 171 therein for decreasing the lateral strength of each fin 150 thereby to facilitate bending over of each fin 150 laterally thereof when the electrode assembly 126 is inserted into a heart chamber such as into a ventricle.

The opening 170 preferably has a diameter of approximately 0.014 inch and is located outwardly and rearwardly of opening 171 which has a diameter of approximately 0.028 inch. Each fin 150 has a thickness of between 0.01 and 0.03 inch and preferably is approximately 0.02 inch thick.

Although similar in construction to the electrode assembly 26 shown in FIG. 1, the electrode assembly 126 shown in FIGS. 4 and 5 has a somewhat different configuration.

In this respect, three fins 150 are provided and are circumferentially spaced from each other about the axis of the sleeve 140 at angles of approximately 120° as opposed to two tines 71, 72 circumferentially spaced 90° from each other.

Referring now more particularly to FIG. 5, each fin 150 is made of a flexible elastomeric material having a relatively thin width, such as for example, 0.02 inch as stated above, and has an upper or top edge 172 extending angularly outwardly and rearwardly from the tip 132 of the tip electrode 130. A base portion 174 of the fin 150 extends along and is integral with outer surface 176 of the sleeve 140.

Finally, the fin 150 is defined by a rear edge, e.g., edge 178, which extends generally radially outwardly from the axis of the sleeve 140.

As shown, the rear edge 178 is defined by a first straight edge portion 180 extending from the outer surface 176 of the sleeve 140, an arcuate partially circular concave or curved surface portion 184 and a further straight edge portion 186 which meets with the top edge 172 and forms a point therewith.

As with the projections or tines 71 and 72 shown in FIGS. 1-3, each fin 150 has at least one saw tooth formation 191, simply defined hereinafter as saw tooth 191, extending from the top edge 172. Preferably as shown, four saw teeth 191-194 extend upwardly from top edge 172.

The top edge 172 of each fin 150 extends at an angle of between 15° and 45° from the axis of the sleeve 140 and is preferably at an angle of approximately 30° as shown.

Then, each saw tooth 186 has a rear edge, e.g., edge 198, which extends outwardly from the top edge, e.g., edge 173, radially outwardly from the axis of the sleeve 140, i.e., at an angle of 90° to the axis of the sleeve 140. Then, a top edge, e.g., edge 200, of each saw tooth 191-194 extends at an angle of between 10° and 30° to the top edge 172 and preferably at an angle of approximately 10° as shown. The points of the saw teeth 191-194 are separated from each other along a line intersecting the points by a distance of approximately 0.05 inch and the back edge 198 of the saw tooth 191 is located approximately 0.025 inch along the top edge 172 from the rear edge surface 186 of the fin 150.

With the construction of the fin 150 defined above, it will be noted that the back edge 198 of each saw tooth 191-194 forms an angle of approximately 60° with the top edge 172 of each fin 150. In this embodiment, the total length of the fin 150 along the base portion 174 of the fin 150 is approximately 0.018 inch.

The dimensions and parameters of the fin 150 described above were determined from empirical tests and have been found to provide the good results desired. Namely, these dimensions and parameters provide a fin 150 which adequately and sufficiently engages trabeculae in a ventricle for holding the electrode assembly 126 in a desired position where the tip 132 of the tip electrode 130 bears against and makes good electrical contact with an endocardial wall in the ventricle.

It will be apparent from the foregoing description that the distal electrode assembly mounted at the distal end of an endocardial lead and having projections with saw tooth formations thereon constructed according to the teachings of the present invention provide a number of advantages, some of which have been described above and others of which are inherent in the invention.

Also it will be apparent from the foregoing description that modifications can be made to the distal electrode assembly of the present invention without departing from the teachings of the present invention. Accordingly, the scope of the present invention is only to be limited as necessitated by the accompanying claims.

I claim:

1. An endocaridal pacing lead comprising: an elongate electrical conductor extending substantially the length of said lead; an insulating sheath surrounding said conductor for substantially the entire length of said conductor; an electrode assembly at the distal end of said lead; said electrode assembly comprising a tip electrode having a distal tip and a proximal end and a sleeve of insulating material surrounding said proximal end of said tip electrode; said elongate conductor being electrically connected to said proximal end of said tip electrode; said sleeve having at least two circumferentially spaced projections which are made of a flexible elastomeric material that is sufficiently pliant to prevent penetration of heart tissue and which project outwardly from said sleeve, each projection extending radially and axially away from the outer surface of said sleeve, outwardly from the axis of said sleeve and rearwardly away from said distal tip; and each projection having a rear edge and a saw tooth formation defined by at least two saw teeth which extend radially outwardly of the axis of said electrode assembly and outwardly from an outer side edge or surface of said projection facing radially away from said lead and each tooth having a rear edge, whereby, when said electrode assembly at the distal end of said lead is implanted with a heart, said rear edges of said projections and of said teeth of said saw tooth formations engage trabeculae within a heart cavity thereby to aid in retaining said distal tip of said tip electrode in good electrical conductive engagement with a desired wall portion in the heart cavity.

2. The lead of claim 1 wherein said projections are spaced circumferentially 90° on the outer surface of said sleeve.

3. The lead of claim 1 wherein each projection extends along an axis which is coplanar with a plane extending through said sleeve and said sleeve axis.

4. The lead of claim 1 wherein each projection has at least three saw teeth.

5. The lead of claim 4 wherein each projection has at least four saw teeth.

6. The lead of claim 1 wherein each projection is an elongate, thin, generally round-in-cross-section tine.

7. The lead of claim 6 wherein each tine has a diameter of between 0.020 and 0.040 inch and, each of said at least two saw teeth extends from the axis of said tine between 0.020 and 0.040 inch and each tine has a length of between 0.20 and 0.30 inch.

8. The lead of claim 6 wherein each tine has a length of approximately 0.24 inch along a line.

9. The lead of claim 6 wherein each tine has four saw teeth and the points of said saw teeth are separated from each adjacent point by approximately 0.05 inch along a line passing through said points.

10. The lead of claim 6 wherein each tine extends along an axis that is at an angle of between 20° and 60° to the axis of said sleev and the back edge of said tine is at an angle of between 45° and 90° to the axis of said tine.

11. The lead of claim 6 wherein the upper inclined surface of each of said at least two saw teeth is between 15° and 30° to the axis of said tine and the back edge of each of said at least two saw teeth is at an angle of between 45° and 90° to the axis of said tine.

12. The lead of claim 6 wherein the forward end of said tine integral with and extending from said sleeve starts at a point on said sleeve approximately one quarter to one third of the length of said sleeve from the forward edge of said sleeve.

13. The lead of claim 6 wherein the base of said tine has a fillet or round surface connecting the upper side of said tine and said sleeve outer surface and a fillet or round surface connecting the lower side of said tine and said sleeve.

14. The lead of claim 1 wherein said sleeve has a length of between 0.17 and 0.30 inch and has a thickness of between 0.02 and 0.04 inch.

15. The lead of claim 1 wherein said sleeve has at least three of said projections extending therefrom.

16. The lead of claim 1 wherein each projection is circumferentially spaced from an adjacent projection by approximately 120°.

17. The lead of claim 16 wherein each of said projections is in the form of a fin having a relatively thin width and an upper edge extending angularly outwardly and rearwardly from said distal tip, and a rear edge extending generally radially outwardly from the axis of said sleeve.

18. The lead of claim 1 wherein each of said projections is in the form of a fin made of a flexible material having a relatively thin width and an upper edge extending angularly outwardly and rearwardly from the electrode tip and a rear edge extending generally radially outwardly from the axis of said sleeve.

19. The lead of claim 18 wherein each fin has at least one opening therein to render same more flexible.

20. The lead of claim 18 wherein said rear edge of said fin has a concave edge surface.

21. The lead of claim 18 wherein said fin has a top edge from which each of said at least two saw teeth extend and said top edge being at an angle of between 20° and 45° to the axis of said sleeve.

22. The lead of claim 21 wherein the upper surface of each of said at least two saw teeth is at an angle of between 10° and 30° to the plane containing said top edge surface of said fin.

23. The lead of claim 18 wherein each of said at least two saw teeth has a rear edge which extends along a line generally radially outwardly from the axis of said sleeve perpencidular to said axis and forms an angle of approximately 60° with said top edge of said fin.

24. The lead of claim 18 wherein said fin has a thickness of between 0.010 and 0.030 inch.

25. The lead of claim 18 wherein each fin has at least three saw teeth extending from the upper edge surface thereof.

26. The lead of claim 25 wherein said fin has four saw teeth extending from the top edge surface thereof.

27. An electrode assembly for connection to the distal end of an endocardial pacing lead, said assembly comprising a tip electrode including a distal tip portion and a proximal end portion, and a sleeve of insulating material surrounding said proximal end portion and having two spaced apart flexible elastomeric tines which are sufficiently pliant to prevent penetration of heart tissue and which project outwardly from said sleeve, each tine extending in a direction which is radially and axially away from the outer surface of said sleeve and from said distal tip portion, and each tine having a rear edge and a saw tooth formation defined by at least two saw teeth which extend radially outwardly of the axis of said electrode and outwardly from an outer side edge of said tine facing radially away from said lead, whereby, when said electrode assembly is implanted within a heart, said rear edges of said tines and of said teeth of said saw tooth formations engage trabeculae within a heart cavity thereby to aid in retaining said distal tip of said tip electrode in good electrical conductive engagement with a desired wall portion in a heart cavity.

28. An electrode assembly for connection to the distal end of an endocardial pacing lead, said assembly comprising a tip electrode including a distal tip portion and a proximal end portion, and a sleeve of insulating material surrounding said proximal end portion and having two spaced apart flexible elastomeric fins which are sufficiently pliant to prevent penetration of heart tissue and which project outwardly from said sleeve, each fin extending in a direction which is radially and axially away from the outer surface of said sleeve and rearwardly from said distal tip portion, and each fin having a rear edge and a saw tooth formation defined by at least two saw teeth which extend radially outwardly of the axis of said electrode and outwardly from an outer side edge of said fin facing radially away from said lead, whereby, when said electrode assembly is implanted with a heart, said rear edges of said fins and of said teeth of said saw tooth formations engage trabeculae within a heart cavity thereby to aid in retaining said distal tip of said tip electrode in good electrical conductive engagement with a desired wall portion in a heart cavity.

* * * * *

UNITED STATES PATENT AND TRADEMARK OFFICE
CERTIFICATE OF CORRECTION

PATENT NO.  : 4,841,971
DATED       : June 27, 1989
INVENTOR(S) : Stanley R. Hess It is certified that error appears in the above-identified patent and that said Letters Patent is hereby corrected as shown below:

Column 2, line 22 "disal" should be --distal--

Column 4, line 67 "i na" should be --in a--

Column 6, line 8 "10°" should be --20°--

Column 7, line 23 "line" should be

--line parallel to the axis of said tine and extending from a line perpendicular to the tine axis and passing through the rearwardmost point of said rear edge of said tine through the point of each of said at least two saw teeth to a point where said line meets the outer surface of said sleeve forwardly of the base of said tine on said sleeve--

Signed and Sealed this

Tenth Day of November, 1992

Attest:

DOUGLAS B. COMER

*Attesting Officer*     *Acting Commissioner of Patents and Trademarks*